(12) United States Patent
Wang

(10) Patent No.: US 8,802,126 B2
(45) Date of Patent: *Aug. 12, 2014

(54) POLYESTER IMPLANTABLE MEDICAL DEVICE WITH CONTROLLED IN VIVO BIODEGRADABILITY

(75) Inventor: Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 848 days.

This patent is subject to a terminal disclaimer.

(21) Appl. No.: 12/165,092

(22) Filed: Jun. 30, 2008

(65) Prior Publication Data

US 2009/0324670 A1 Dec. 31, 2009

(51) Int. Cl.
  *A61F 2/00* (2006.01)
  *A61K 9/00* (2006.01)
  *A61K 9/16* (2006.01)
  *A61L 27/26* (2006.01)

(52) U.S. Cl.
  CPC ............. *A61K 9/0024* (2013.01); *A61K 9/1647* (2013.01); *A61L 27/26* (2013.01)
  USPC ........................................................ 424/426

(58) Field of Classification Search
  None
  See application file for complete search history.

(56) References Cited

U.S. PATENT DOCUMENTS

| | | | |
|---|---|---|---|
| 5,705,181 A | 1/1998 | Cooper et al. | |
| 2003/0144730 A1 | 7/2003 | Datta et al. | |
| 2004/0022859 A1* | 2/2004 | Chen et al. | 424/486 |
| 2004/0052992 A1 | 3/2004 | Boone et al. | |
| 2005/0037075 A1* | 2/2005 | Farokhzad et al. | 424/468 |
| 2006/0057179 A1* | 3/2006 | Giroux | 424/422 |
| 2007/0003625 A1* | 1/2007 | Seo et al. | 424/486 |
| 2007/0059363 A1* | 3/2007 | Lee et al. | 424/468 |
| 2007/0149640 A1 | 6/2007 | Andjelic et al. | |

FOREIGN PATENT DOCUMENTS

| | | |
|---|---|---|
| EP | 0 787 755 | 8/1997 |
| WO | WO 00/01426 | 1/2000 |
| WO | WO 01/45763 | 6/2001 |
| WO | WO 2004/011054 | 2/2004 |
| WO | WO 2007/020430 | 2/2007 |
| WO | WO 2007/078718 | 7/2007 |

OTHER PUBLICATIONS

Resomer (Sigma aldrich) (http://www.sigmaaldrich.com/materials-science/polymer-science/resomer.html), p. 1-2.*
Andjelič et al., "Bimodal Molecular Weight Polyesters", Polymeric Materials: Science & Engineering vol. 51, pp. 821-822 (2006).
Bao et al., "Polymer inking as a micro-and nanopatterning technique", J. Vac. Sci. Tech. B 21, No. 6, pp. 2749-2754 (2003).
Cloizeaux "Double Reptation vs. Simple Reptation in Polymer Melts", Europhys. Lett. 5 (5), pp. 437-442 (1988).
Dorgan et al., "Melt rheology of variable L-content poly(lactic acid)", J. of Rheology vol. 49, issue 3, Abstract, 1 pg. (2005).
Kawamoto et al., "Nucleating, Agent for Poly(L-lactic acid)—An Optimization of Chemical Structure of Hydrazide Compound for Advanced Nucleation Ability", J. of Applied Polymer Science, vol. 103, pp. 198-203 (2007).
Mauduit et al., "Hydrolytic degradation of films prepared from blends of high and low molecular weight poly(DL-lactic acid)s", J. of Biomedical Mat. Res. vol. 30, pp. 201-207 (1996).
Nichetti et al., "Viscosity model for polydisperse polymer melts", J. Rheol. 42 (4), pp. 951-969 (1998).
Von Recum et al, "Degradation of polydispersed poly(L-lactic acid) to modulate lactic acid release", Biomat. 16, pp. 441-445 (1995).
International Search Report for PCT/US2009/048164, mailed Jul. 15, 2010, 5 pgs.
Zilberman et al., "Drug-Eluting Bioresorbable Stents for Various Applications", Annu. Rev. Biomed. Eng. 8, pp. 153-180 (2006).

* cited by examiner

*Primary Examiner* — Bethany Barham
(74) *Attorney, Agent, or Firm* — Squire Patton Boggs (US) LLP

(57) ABSTRACT

This invention relates to blends of high, optionally medium, and low molecular weight polyesters where at least the low molecular weight polyester is substituted with an acidic moiety, the biodegradation of the blends being controllable by selection of the mean molecular weigh of each fraction, the quantity of each fraction in the blend and the amount and pKa of the acidic moiety(ies).

27 Claims, No Drawings

POLYESTER IMPLANTABLE MEDICAL DEVICE WITH CONTROLLED IN VIVO BIODEGRADABILITY

FIELD

This invention relates to organic chemistry, polymer chemistry, material science and medical device technology. In particular it relates to polyester implantable medical devices with controllable in vivo biodegradation properties.

BACKGROUND

Until the mid-1980s, the accepted treatment for atherosclerosis, i.e., narrowing of the coronary artery(ies) was by-pass surgery. While effective and while having evolved to a relatively high degree of safety for such an invasive procedure, by-pass surgery still involves potentially serious complications and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a very short time compared to by-pass surgery and the recovery time was minimal. However, PTCA brought with it other problems such as vasospasm and elastic recoil of the stretched arterial wall which could undo much of what was accomplished and, in addition, it created a new disease, restenosis, the re-clogging of the treated artery due to neointimal hyperplasia.

The next improvement, advanced in the mid-1980s was the use of a stent to maintain the luminal diameter after PTCA. This for all intents and purposes put an end to vasospasm and elastic recoil but did not entirely resolve the issue of restenosis. That is, prior to the introduction of stents, restenosis occurred in from 30-50% of patients undergoing PTCA. Stenting reduced this to about 15-20%, much improved but still more than desirable.

In 2003, drug-eluting stents or DESs were introduced. The drugs initially employed with the DES were cytostatic compounds, that is, compounds that curtailed the proliferation of cells that resulted in restenosis. The occurrence of restenosis was thereby reduced to about 5-7%, a relatively acceptable figure. However, the use of DESs engendered a new problem, late stent thrombosis, the forming of blood clots long after the stent was in place. It was hypothesized that the formation of blood clots was most likely due to delayed healing, a side-effect of the use of cytostatic drugs.

Generally speaking, stents achieve their optimal beneficial effect within 24 months of implantation and sometimes substantially less. Because of the materials of which stents are constructed, however, they tend to have much longer in vivo life spans, which tends to contribute to late stent thrombosis. This is of course true of very biostable metallic stents but it holds as well for most polymeric stents. While polymers that biodegrade relatively rapidly, easily in 24 months or less, are known, they generally do not exhibit the physical properties required of stents like strength, toughness, ductility and the like, while polymers that do exhibit these characteristics tend to have much longer biodegradation times.

What is needed is a polymeric implantable medical device that exhibits all the physical characteristics desired in such devices while also being essentially fully biodegradable over a clinically relevant timeframe. The present invention provides such implantable devices.

SUMMARY

Thus, in one aspect the invention relates to an implantable medical device, comprising:
a blend of a high molecular weight polyester and a low molecular weight polyester, wherein
  the high molecular weight polyester has a molecular weight of about 200,000 Da to about 1,000,000 Da;
  the low molecular weight polyester has a molecular weight of about 200 Da to about 20,000 Da;
  the low molecular weight polyester comprises about 0.1% w/w to about 5% w/w of the blend; and,
  the low molecular weight polyester comprises an acidic moiety.

In an aspect of this invention, the acidic moiety is selected from the group consisting of a carboxylic acid, a sulfinic acid, a sulfonic acid and a phosphonic acid.

In an aspect of this invention, the acidic moiety is a carboxylic acid.

In an aspect of this invention, the high molecular weight polyester comprises an acidic moiety.

In an aspect of this invention, the acidic moiety of the high molecular weight polyester is the same as the acidic moiety of the low molecular weight polyester.

In an aspect of this invention, the blend further comprises a medium molecular weight polyester having a molecular weight of about 20,000 DA to about 200,000 Da.

In an aspect of this invention, the medium molecular weight polyester comprises an acidic moiety selected from the group consisting of a carboxylic acid, a sulfinic acid, a sulfonic acid, a phosphonic acid and combinations thereof.

In an aspect of this invention, the acidic moiety of the medium molecular weight polyester is the same as the acidic moiety of the low molecular weight polyester.

In an aspect of this invention, the low molecular weight polyester comprises from about 0.2% w/w to about 5% w/w of the blend.

In an aspect of this invention, the medium molecular weight polyester comprises about 2% w/w to about 20% w/w of the blend.

In an aspect of this invention, the medium molecular weight polyester comprises about 2% w/w to about 20% w/w of the blend.

In an aspect of this invention, the medium molecular weight polyester comprises about 5% w/w to about 10% w/w of the blend.

In an aspect of this invention, the high molecular weight polyester has a molecular weight from about 300,000 Da to about 700,000 Da.

In an aspect of this invention, the low molecular weight polyester has a molecular weight of about 500 Da to about 10,000 Da.

In an aspect of this invention, the medium molecular weight polyester has a molecular weight of about 50,000 Da to about 100,000 Da.

In an aspect of this invention, the high molecular weight polyester and the low molecular weight polyester are independently selected from the group consisting of poly(L-lactide), poly(D-lactide), poly(L-lactide-co-ε-caprolactone), poly(D-lactide-co-ε-caprolactone), poly(L-lactide-co-trimethylene carbonate), poly(D-lactide-co-trimethylene carbonate) and combinations thereof.

In an aspect of this invention, the high molecular weight polyester and the low molecular polyester are the same polyester.

In an aspect of this invention, the polyester is poly(L-lactide) or poly(D-lactide).

In an aspect of this invention, the medium molecular weight polyester is the same as the high molecular weight and the low molecular weight polyester.

In an aspect of this invention, the high molecular weight polyester, the medium molecular weight polyester and the low molecular weight polyester are all poly(L-lactide) or poly(D-lactide).

In an aspect of this invention, the implantable medical device comprises stent.

In an aspect of this invention, the stent is a vascular stent.

In an aspect of this invention the vascular stent degrades substantially completely in about 8 to about 24 months.

In an aspect of this invention, the stent biodegrades substantially completely in about 10 to about 16 months.

In an aspect of this invention, the implantable medical device comprises a nanoparticles or a microparticle.

In an aspect of this invention, the nanoparticles or microparticle comprises a therapeutic agent encapsulated therein.

DETAILED DESCRIPTION

Use of the singular herein includes the plural and vice versa unless expressly stated or unambiguously obvious from the context to be otherwise. That is, "a" and "the" refer to one or more of whatever the word modifies. For example, "a carboxylic acid moiety" may refer to one, two, three or more such moieties. Likewise, "the medium molecular weight polyester" may refer to one, two or more different medium molecular weight polyesters. By the same token, words such as, without limitation, "therapeutic agents" and "polymers" would refer to one therapeutic agent or one polymer as well as to a plurality of such agents or polymers, again, unless it is expressly stated or obvious from the context that such is not intended.

As used herein, a condition or event modified by the words "substantial" or "substantially" means that, while not exactly what the condition or event would be understood to be if unmodified, it would be considered close enough by those of ordinary skill in the art to warrant designating the condition or event as being extant. Thus, for the purpose of this invention, an implantable medical device that is stated to "biodegrade substantially completely" over a given time period means that, while vestiges of the device may remain, those remnants do not exhibit any of the physical characteristics of the intact device and in fact may not be located at exactly the same position in a patient's body as that to which it was initially deployed. Further, the remnants would be of a size and quantity so as to not participate in the creation of late-stent thromboses.

The use of other words or approximation herein, such as "about" or "approximately" when used to describe numerical values or ranges likewise are understood to mean that those skilled in the art would readily consider a value different from the exact number or outside the actual range to be close enough to come within the aegis of that number or range. At the very least, "about" or approximately is understood to mean±15% of a given numerical value or range starting and ending point.

As used herein, "optional" means that the element so-modified may or may not be present.

As used herein, "biodegradable" refers to any natural means by which a polymer can be disposed of in a patient's body. This includes such phenomena as biological decomposition, bioabsorption, resorption, etc. Biodegradation of a polymer in vivo results from the action of one or more endogenous biological agents and/or conditions such as, without limitation, enzymes, microbes, other cellular components, physiological pH and temperature and the like. Bioabsorbable or bioresorbable on the other hand generally refers to the situation wherein the polymer itself or its degradation products are removed from the body by cellular activity such as, without limitation, phagocytosis. Bioerodible refers to both physical processes such as, without limitation, dissolution and chemical processes such as, without limitation, backbone cleavage by hydrolysis of the bonds linking constitutional units of a polymer together. As used herein, biodegradable includes bioerodible, bioresobable and bioabsorbable.

Biodegradable polymers are preferred for many applications because their ability to decompose in a biological environment confers on them a number of desirable characteristics. For example, the fact that a polymer will biodegrade and can eventually be essentially completely eliminated from a patient's body can avoid the need to invasively remove a device, e.g., a DES, after its job is done. In addition, by judicious choice of biodegradable polymer, e.g., selecting one that bioerodes by bulk erosion, one that bioerodes by surface erosion or some combination thereof, the properties of the polymer can be used as an added tool for fine-tuning the release rate of a drug from a device or a coating on a device.

Of course, if a polymer is going to degrade in a patient's body, it is imperative that it be biocompatible, that is, that its degradation products do no harm to the patient. As used herein, "biocompatible" refers to a polymer that both in its intact, as initially synthesized and deployed, state, and its biodegradation products, are not, or at least are minimally, toxic to living tissue; do not, or at least minimally and reparably, injure(s) living tissue; and/or do not, or at least minimally and/or controllably, cause(s) an immunological reaction in living tissue. To achieve this characteristic requires careful attention to the chemistry of the polymer and its degradation products. A great deal of work has gone into the effort to find suitable biodegradable polymers and one class of such polymers that has exhibited particularly desirable properties in terms of biocompatibility and biodegradation as well as other physical characteristics that can be engineered into the polymer by judicious selection their constitutional units are polyesters.

As used herein, "polyester" refers to a polymer that has as its predominant main chain or "backbone" structural characteristic an ester, —C(O)O—, moiety. Thus the generic structure of a polyester can be depicted in the following manner: —[RC(O)ORC(O)O]$_n$—, wherein R comprises a hydrocarbon entity such as alkyl, cycloalkyl, alkenyl, alkynyl and aryl groups, any of which may be further substituted with one or more functional groups. For the purposes of this invention, polyesters also includes polycarbonates, i.e., the above structure wherein R is —R'O—, that is the generic structure becomes: —[R'OC(O)OR'OC(O)O]$_n$—, and polythioesters in which one or more of the oxygen atoms of the ester or carbonate moiety is replaced by sulfur.

A polymer of this invention may be a homopolymer, a copolymer, a star polymer, a dendritic polymer (dendrite) or a graft polymer, although presently preferred are homopolymers and copolymers.

A homopolymer simply refers to a polymer comprising a single monomer, a monomer simply being a molecule that is iteratively reacted with itself to form chains of constitutional units, i.e., a polymer. A copolymer refers to a polymer prepared from two or more monomers that may be reacted so as to form random copolymers, regular alternating copolymers, random alternating copolymers, regular block copolymers or random block copolymers. A random copolymer has the general structure, assuming three monomers/constitutional units, x-x-y-x-z-y-y-x-z-y-z- . . . , while a regular alternating copolymer has the general structure: . . . x-y-z-x-y-z-x-y-z- . . . and a random alternating copolymer has the general structure: . . . x-y-x-z-x-y-z-y-z-x-y- . . . , it being understood that the juxtaposition of constitutional units shown here is for purpose of illustration only and a copolymer of this invention may vary from that shown. A regular block copolymer has the general structure: . . . x-x-x-y-y-y-z-z-z-x-x-x . . . , while a random block copolymer has the general structure: . . . x-x-x-z-z-x-x-y-y-y-z-z-z-x-x-z-z-z- . . . . Similarly to random and regular and alternating copolymers, the juxtaposition of blocks, the number of constitutional units in each block and the number of blocks in a block copolymer of this invention are not in any manner limited by the preceding illustrative generic structures. In fact, presently preferred polymers of this invention are either homopolymers or two-monomer copolymers but the general principles above still pertain.

Presently preferred polyesters include poly(l-lactide), poly(d-lactide), poly(l-lactide-co-ε-caprolactone), poly(d-lactide-co-ε-caprolactone), poly(l-lactide-co-trimethylene carbonate) and poly(d-lactide-co-trimethylene carbonate).

A "star" polymer refers to the product of the reaction of a small multifunctional core molecule with one or more difunctional molecules to create a branched configuration:

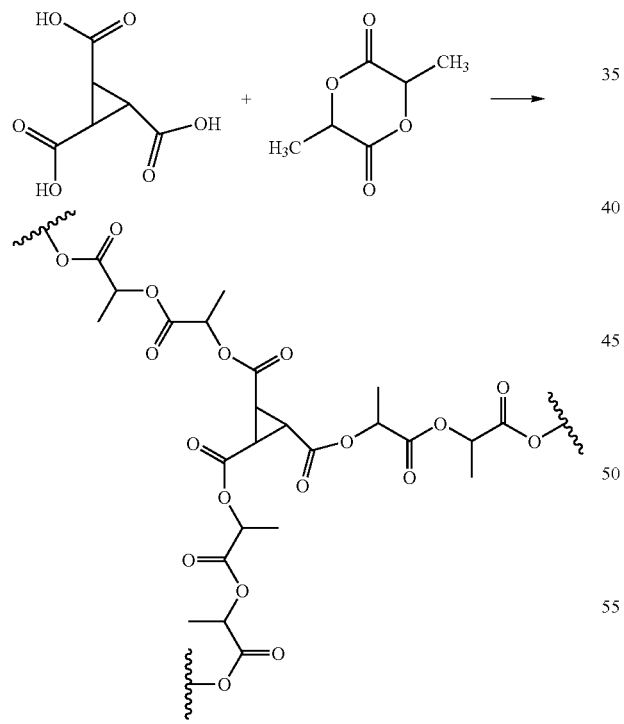

A dendritic polymer refers to a star-like polymer in which the constitutional units emanating from the core structure are themselves multifunctional (3 or more functional groups) such that branching continues throughout the polymerization process. That is, a dendritic polymer can be schematically represented as:

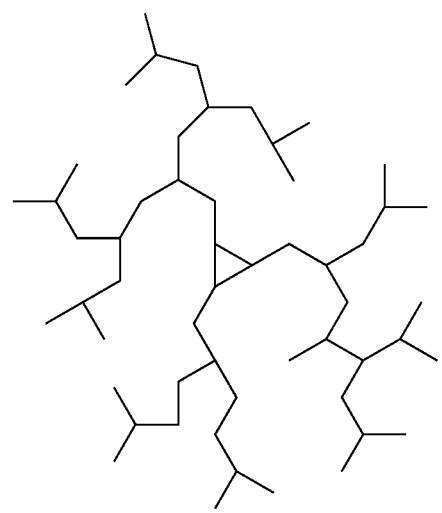 [SMILES: CC(C)CCC(CCC(C)C)CC1C(CC(CC(CC(C)C)CC(C)C)CC(CC(C)C)CC(C)C)C1CC(CC(C)C)CC(C)C(CC(C)C)C(C)C]

wherein each level of branching is called a "generation." That is, the schematic dendrite shown above would be considered a third generation dendrite.

Of course, the use of the cyclopropane core unit which results in three branches initially for the illustrative star polymer and dendrimer above is non-limiting; the core unit may be more or less branches and need not be cyclic; neither star polymers nor dendrimers are so limited.

A graft polymer simply refers to a macromolecule to which additional polymeric moieties are attached to a main backbone structure as side chains, the side chains generally having constitutional or configurational features that differ from those of the main chain:

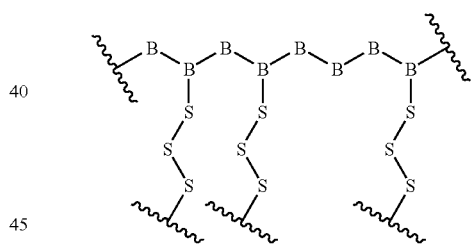

wherein the sequence of "B" groups constitutes the main or backbone chain and the "S" groups constitute the side chain or grafted entity.

As used herein a "constitutional unit" refers to the repeating structure in a polymer backbone, the constitutional unit resulting from the reaction of monomers. For example, without limitation, a poly(l-lactide), which is a presently preferred polymer of this invention, is prepared by the polymerization of the monomer l-lactide:

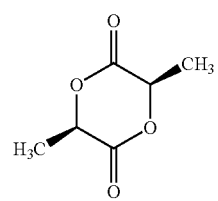

while the constitutional unit derived therefrom is

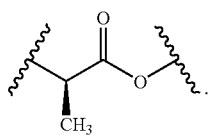 [SMILES: *OC(=O)[C@H](*)C]

A polyester of this invention may be high, medium or low molecular weight. The terms "high," "medium" and "low" are intended to be relative terms. That is, a polyester of arbitrary molecular weight 150,000 Da may constitute any of the three levels of molecular weight polymers. For example, if the 150,000 Da polyester is paired with two other polyesters of molecular weight 200,000 Da and 300,000 Da, then it would obviously be the "low" molecular weight polyester. If, on the other hand, it were to be paired with a 125,000 Da and a 20,000 Da polyester, it would comprise the "high" molecular weight polyester and so on.

It is presently preferred that the molecular weight of polymers of this invention be reported as the so-called "number average molecular weight," which is calculated by dividing the weight of a sample of polymer by the total number of polymer molecules making up that sample.

The molecular weight may, however, be determined as a "weight average molecular weight" so long as the molecular weight of all polymer fractions are determined by the same method. The weight average molecular weight is determined by dividing the total number of polymer molecules times the weight of each molecule squared by the total number of molecules times the weight of each molecule.

Seeing as the weight average molecular weight is proportional to the square of the individual molecular weights, it is always greater than the number average molecular weight. If the weight average molecular weight is divided by the number average molecular weight for any polymer fraction, a number referred to as the polydispersity index, PI, is obtained. The PI is a measure of the range of individual molecular weights that averages out to give the stated mean molecular weight. As the weight average molecular weight approaches the number average molecular weight, the PI approaches 1, 1 being indicative of a perfectly monodisperse polymer in which each molecule has exactly the same molecular weight. For the purposes of this invention, the PI may vary from close to 1 to virtually as high as can be achieved.

For the purposes of this invention, a high molecular weight polyester of has a number average molecular weight of about 200,000 Da to about 1,000,000 Da, preferably at present about 300,000 Da to about 700,000 Da. A medium molecular weigh polyester of this invention has a molecular weight of about 20,000 Da to about 200,000 Da, preferably at present about 50,000 Da to about 100,000 Da. A low molecular weight polyester of this invention has a molecular weight of about 200 Da to about 20,000 Da, preferably at present about 500 Da to about 10,000 Da.

The high and low molecular weight polyesters are blended together to form a composition of this invention. By "blended" is simply meant that they are mixed together until a homogenous mass of material is obtained whereby a sample taken from any location in the final blend will have the same percent low molecular weight polyester as a sample taken from any other location in the blend. If a medium molecular weight polyester in included in the blend, it also would be mixed with the high and low molecular weight polyesters until a sample taken at any location in the blend would have the same percent of low and medium weight polyester as a sample taken from any other location in the blend.

It is preferred that the weight percent (w/w) of low molecular weight polyester in a blend of this invention be about 0.1% to about 5%, preferable at present, about 0.2% to about 2%.

If a medium molecular weight polyester is include in the blend, it is preferred that its weight percent by about 2% to about 20%, preferably at present about 5% to about 10%.

At least a portion of the low molecular weigh polyester of this invention is functionalized with an acidic moiety. By "at least a portion" is meant that at least 20% but a high as 100% of the low molecular weight polyester molecules must be substituted with at least one acidic moiety. Preferably at present about 50% to about 100% are so functionalized. The percentage functionalization is readily obtainable by mixing 100% functionalized (or as close to 100% as is experimentally attainable) polyester by weight with non-functionalized polyester to arrive at the desired percentage. For the purposes of this invention an "acidic moiety" is any group that exhibits a pKa below about 6, which includes, without limitation, carboxylic acids, —CRR'C(O)OH, sulfinic acids, —CRR'S(O)OH, sulfonic acids, CRR'S(O)$_2$OH and phosphonic acids, —CRR'P(O)$_3$OH. R and R' are groups that modulate the pKa of the acidic moiety such as, without limitation, halo (fluorine, chlorine, bromine, iodine), nitro (NO$_2$), alkyl and aryl groups. By judicious choice of R and R', the pKa and therefore the effect on the polyester of the acidic moiety can be fine-tuned to a selected value. The effect of various substituents on the pKa of an acidic moiety is well-known in the art and based on the disclosures herein those skilled in the art will have no trouble manipulating the pKa of an acidic moiety of this invention to achieve whatever polyester degradation rate they desire.

The acidic moiety may be covalently bonded at any location along the backbone of the polymer, either directly or through a linker group. A "linker" simply refers to any group that is covalently bonded to the backbone of the polyester at one position and to an acid moiety (or an acidic moiety precursor) at a different position. For example, without limitation, any of the following could be a "linker" for the purposes of this invention: —X(CH$_2$)$_n$C(O)OH, —XCH$_2$CH$_2$(OCH$_2$CH$_2$)$_n$CH$_2$CH$_2$C(O)OH, —XC(O)CH$_2$CH$_2$C(O)OH and

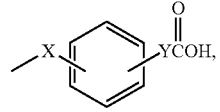

where X, through which the linker is bonded to the polymer backbone, can be oxygen, nitrogen or sulfur.

Preferably at present the acidic moiety(ies) are located at the termini of the polymer chains. It is well-known in the art how to prepare polyesters that have hydroxyl groups at either or both ends of the individual chains, e.g., without limitation:

RO—[C(O)CH(CH$_3$)O]$_n$C(O)CH(CH$_3$)OH wherein the R group may be a protective group that can be removed after the polymerization is complete to reveal a second hydroxyl group. Such protective groups are well known in the art and will not be further discussed here. The particular hydroxy-terminated polyester shown above is a hydroxy-terminated polylactide (PLA-OH), which, while a useful polymer of this invention, is not in any manner intended nor it is to be construed to limit the scope hereof. The conversion of the hydroxy-terminated polymer to a carboxy-terminated polymer can be accomplished by any number of procedures such as, without limitation, reaction with succinic anhydride:

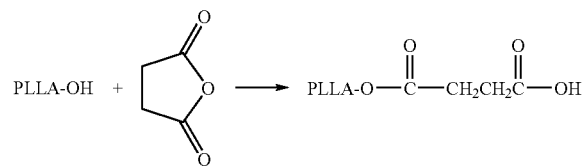

Those skilled in the art will envision other procedures for bonding a carboxyl group to the polymer backbone based on the discussion herein; all such procedures are within the scope of this invention.

Sulfinic, sulfonic and phosphonic acidic moieties may be formed similarly. For example, without limitation, benzene sulfinic, sulfonic and phosphonic acids are well-known in the art and in fact are commercially available. These may be chloromethylated, for example without limitation, by reaction with formaldehyde and hydrochloric acid and the chloromethylated derivative reacted with the hydroxyl end-groups of the polyester to afford the desired acidic moiety-containing polyester.

While at least a fraction of the low molecular weight polyester of a blend of this invention must include an acidic moiety, all or part of the high and medium molecular weight polyesters may independently optionally also comprise an acidic moiety. In this regard, if the medium molecular weight polyester does comprise an acidic moiety it is preferred that about 20% to about 100%, preferably at present about 50% to about 100% of the medium molecular weight polyester be so functionalized.

With regard to the high molecular weight polyester, if it is optionally functionalized with an acid moiety, it is preferred that about 20% to about 100%, preferably about 50% to about 100% of the high molecular weight polyester be so functionalized.

Arriving at the desired percentage acidic moiety for medium and high molecular weight polyesters is accomplished in the same manner as set forth about with regard to low molecular weight polyesters.

Further, if more than just the low molecular weight polyester fraction is substituted with an acidic moiety, the acidic moiety on the other fractions may be the same as or different than the acidic moiety on the low molecular weight fraction and the same as or different that the acidic moiety on each other.

The polyester blends of this invention may comprise one specific polyester as the high and low or high, medium and low molecular weight polymers; e.g., all might, without limitation, be poly(l-lactide)s. Or one or two of the polyesters may be of one sort while the third may be of another; e.g., without limitation, the high molecular weight polyester may be poly(l-lactide), the medium molecular weight polyester may be poly(l-lactide-co-trimethylene carbonate) and the low molecular weight polyester may be poly(trimethylene carbonate). Further, if desired each molecular weight level may comprise a mixture of polyesters; e.g., without limitation, the high and/or the medium, if present, and/or the low molecular weight polyesters may be mixtures of poly(l-lactide) and poly(d-lactide) or, again without limitation, poly(l-lactide) and poly(trimethylene carbonate). All such mixtures and combinations of polyesters are within the scope of this invention.

As used herein, an "implantable medical device" refers to any construct that is totally or partly introduced, surgically or medically, into a patient's body or by medical intervention into a natural orifice, and which is intended to remain in place until the device biodegrades.

Examples of implantable medical devices are, without limitation, vessel wraps and stents. A vessel wrap is a thin sheet of flexible material, which may be fabric, polymer, metal, etc. that is literally wrapped around the outside of a vessel and is in contact with the outer surface. The wrap may be solid or it may be formed in virtually any manner of desired pattern such as, without limitation, a mesh or a ribbed polymeric structure.

As used herein, a "stent" refers generally to any device used to hold tissue in place in a patient's body. Particularly useful stents, however, are those used for the maintenance of the patency of a vessel in a patient's body when the vessel is narrowed or closed due to diseases including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. A stent can be used in, without limitation, neuro, carotid, coronary, pulmonary, aorta, renal, biliary, iliac, femoral and popliteal arteries as well as other peripheral vasculatures. A stent can be used in the treatment or prevention of diseases such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents, including those of this invention, may be employed for the delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A further example of an implantable medical device of this invention is a nanoparticles or a microparticle in which is embedded a therapeutic agent intended to be released at a desired location in a patient's body.

As used herein, a "nanoparticle" refers to a solid having as its largest cross-sectional, i.e., through the solid as opposed to along its surface, dimension of no greater than 100 nanometers. The solid can have any desired shape although substantially spherical particles are well-known in the art, are readily prepared and are presently preferred. By "substantially spherical" is meant that the particles need not have a surface that mimics a table tennis ball, i.e., virtually perfectly spherical but rather may by odd-shaped but would be considered generally "round" by one of skill in the art.

A microparticle has the same characteristics as a nanoparticles except that its smallest cross-sectional dimension is greater than 100 nm. The maximum size of a microparticle will depend at least in part on the route of administration, e.g., without limitation, oral, subcutaneous implantation, catheter delivery, etc. and will be readily determinable by the skilled artisan As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease;

(2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

Based on the disclosure herein, those skilled in the art will be able to combine the variables of this invention to achieve whatever biodegradation rate they desire, the variables being the mean molecular weight of each fraction, the number of fractions, i.e., high and low molecular weight only or high, medium and low molecular weight, the quantity of each fraction in the blend, the pKa of the acidic moiety and the quantity of acid moiety in the blend, e.g., all of the low molecular weight fraction or just a part of it, whether or not the high and/or medium weight comprise acidic moieties and, if so, the quantity of such acidic moieties in each fraction and the pKa of each of those moieties.

In general, as the pKa of the acidic moiety decreases, that is, as the moiety become more acidic, the rate of degradation of a polyester will increase as it also will with increasing quantities of acid moiety.

Overall, the degradation time of pure high Mw PLLA is about 3 years or more. The degradation time for a pure middle Mw PLLA with acidic moieties would be less than 2 year, possibly less than 1 year depending on the degree of incorporation of acidic moieties in the polymer. The degradation rate of a low Mw PLLA with acidic moieties would be less than 8 months and as low as 4 months or even less, again depending on the degree of acid moiety substitution. Thus, in a non-limiting example, the degradation time of the same high Mw PLLA that in pure state exhibits a degradation time of 3 years can be decreased to less than 1.5 year or even less than 1 year with up to 5% low Mw PLLA having acidic moieties. Based on the disclosures herein, those skilled in the art should be able to create a polyester implantable medical device having virtually any degradation time by adjusting the molecular weights of the two (high and low) or three (high, medium and low) polyesters, the quantity of each in the blend used to make the device, the degree of acidic moiety substitution and the pKa of the acidic moiety(ies).

EXAMPLES

Example 1

Synthesis of PLLA-COOH

PLLA-COOH is synthesized in two steps. First, OH-terminated PLLA (PLLA-OH) is synthesized by the ring-opening polymerization of L-lactide in the presence of various kinds of alcohols. Then, PLLA-COOH is prepared through the acidification of PLLA-OH (see Scheme 1a and 1b).
1a. Synthesis of OH-Terminated Polylactide (PLLA-OH)

L-Lactide and 1-dodecanol are added in a glass ampoule containing a Teflon-coated magnetic stirring bar. After Sn-oct catalyst is added, the ampoule is sealed under a vacuum after being purged three times with nitrogen at 90° C. The ampoule is heated to 130° C. in an oil bath for 5 h with stirring. After the reaction, the product is dissolved in chloroform and micro-filtered through a 0.45-mm-pore membrane filter. The polymer is precipitated into methanol, filtered, and dried under a vacuum. For the synthesis of the star-shaped PLLA-OH, the polymerization is carried out with Sn-oct in the presence of glycerol or pentaerythritol.
1b. Synthesis of COOH-Terminated Polylactide (PLLA-COOH)

The PLLA-OH, succinic anhydride, 4-dimethylaminopyridine (DMAP), and triethylamine (TEA) are dissolved in 1,4-dioxane and stirred overnight at room temperature. 1,4-Dioxane is re-moved under a vacuum, and the residue is dissolved in chloroform and then washed with distilled water three times. After the chloroform layer separated, it is dried over anhydrous $MgSO_4$ and filtered. The polymer is precipitated into methanol, filtered, and dried under a vacuum.

Example 2

Bi-Modal PLLA-COOH System and Stent Preparation

2a. Preparation of Bi-Modal PLLA-COOH System 200 g medium Mw PLLA-COOH (Mw=100 kg/mol) is mixed with 1 kg high Mw PLLA-COOH (Mw=600 kg/mol) at room temperature in a 2 L mechanical blender with stirring speed at 300 rpm for 5-10 min. In order to achieve the best blending effect, a 2 L batch mixer or twin screw compounder can be used to for the blending at 190° C.
2b. Tubing Extrusion The bi-modal PLLA-COOH blend tubing is formed through extrusion in a signal or twin screw extruder at 200° C. The size of the extruded tubing is set at 0.02" for ID and 0.06" for OD.
2c. Stent Preparation Through Laser Cutting and Crimping In case the crystallinity of the extruded PLLA tubing is still not high enough for extruded tubing, it can be expanded in a glass mold at about 90° C. and then be cut into stent by laser.

Example 3

Multi-Modal PLLA-COOH System and Stent Preparation

3a. Preparation of Multi-Modal PLLA-COOH System 10 g low Mw PLLA-COOH (Mw=50 kg/mol), 200 g medium Mw PLLA-COOH (Mw=200 kg/mol) are mixed with 1 kg high Mw PLLA-COOH (Mw=600 kg/mol) through a twin screw compounder at 190° C.
3b. Tubing Extrusion The multi-modal PLLA-COOH blend tubing is formed through extrusion in a signal or twin screw extruder at 200° C. The size of the extruded tubing is set at 0.02" for ID and 0.06" for OD. In case there is no need to use expander to further increase the crystallinity and biaxial orientation, the size of the extruded tubing can be directly set at 0.12" for ID and 0.13" for OD.
3c. Stent Preparation Through Laser Cutting and Crimping The tubing (ID=0.012" and OD=0.013") is directly cut into a stent by laser and crimped to smaller size (0.05") at which time it is ready to use.

In case the crystallinity and orientation of the extruded tubing needs to be further increased, the tubing will be expanded in a glass mold at about 90° C. The expanded tubing will be cut into stent by laser.

What is claimed:

1. A stent, comprising:
   a blend of a high molecular weight polyester and a low molecular weight polyester, wherein
   the high molecular weight polyester has a molecular weight of about 200,000 Da to about 1,000,000 Da;
   the low molecular weight polyester has a molecular weight of about 200 Da to about 20,000 Da;
   the low molecular weight polyester comprises about 0.1% w/w to about 5% w/w of the blend; and,
   at least a portion of the low molecular weight polyester is substituted with an acidic moiety.

2. The stent of claim 1, wherein at least about 20% of the low molecular weight polyester is substituted with an acidic moiety.

3. The stent of claim 1, wherein about 100% of the low molecular weight polyester is substituted with an acidic moiety.

4. The stent of claim 1, wherein the acidic moiety is selected from the group consisting of a carboxylic acid, a sulfinic acid, a sulfonic acid and a phosphonic acid.

5. The stent of claim 4, wherein the acidic moiety is a carboxylic acid.

6. The stent of claim 1, wherein the high molecular weight polyester is substituted with an acidic moiety.

7. The stent of claim 6, wherein the acidic moiety of the high molecular weight polyester is the same as the acidic moiety of the low molecular weight polyester.

8. The stent of claim 1, wherein the blend further comprises a medium molecular weight polyester having a molecular weight of about 20,000 DA to about 200,000 Da.

9. The stent of claim 8, wherein the medium molecular weight polyester is substituted with an acidic moiety selected from the group consisting of a carboxylic acid, a sulfinic acid, a sulfonic acid, a phosphonic acid and combinations thereof.

10. The stent of claim 9, wherein the acidic moiety of the medium molecular weight polyester is the same as the acidic moiety of the low molecular weight polyester.

11. The stent of claim 1, wherein the low molecular weight polyester comprises from about 0.2% w/w to about 5% w/w of the blend.

12. The stent of claim 8, wherein the medium molecular weight polyester comprises about 2% w/w to about 20% w/w of the blend.

13. The stent of claim 12, wherein the medium molecular weight polyester comprises about 5% w/w to about 10% w/w of the blend.

14. The stent of claim 1, wherein the high molecular weight polyester has a molecular weight from about 300,000 Da to about 700,000 Da.

15. The stent of claim 14, wherein the low molecular weight polyester has a molecular weight of about 500 Da to about 10,000 Da.

16. The stent of claim 15, wherein the medium molecular weight polyester has a molecular weight of about 50,000 Da to about 100,000 Da.

17. The stent of claim 1, wherein the high molecular weight polyester and the low molecular weight polyester are independently selected from the group consisting of poly(L-lactide), poly(D-lactide), poly(L-lactide-co-ε-caprolactone), poly(D-lactide-co-ε-caprolactone), poly(L-lactide-co-trimethylene carbonate), poly(D-lactide-co-trimethylene carbonate) and combinations thereof.

18. The stent of claim 17, wherein the high molecular weight polyester and the low molecular polyester are the same polyester.

19. The stent of claim 18, wherein the polyester is poly(L-lactide) or poly(D-lactide).

20. The stent of claim 18, wherein the medium molecular weight polyester is the same polyester as the high molecular weight and the low molecular weight polyester.

21. The stent of claim 20, wherein the high molecular weight polyester, the medium molecular weight polyester and the low molecular weight polyester are all poly(L-lactide) or poly(D-lactide).

22. The stent of claim 1, wherein the stent is a vascular stent.

23. The stent of claim 22, wherein the vascular stent degrades substantially completely in about 8 to about 24 months.

24. The stent of claim 22, wherein the stent biodegrades substantially completely in about 10 to about 16 months.

25. The stent of claim 1, wherein the low molecular weight polyester is substituted with an acidic moiety at its terminus having hydroxyl group.

26. The stent of claim 25, wherein the acidic moiety is a carboxylic acid, wherein the carboxylic acid moiety is linked to the polyester via a linker.

27. The stent of claim 1, wherein the acidic moiety is selected from the group consisting of a sulfinic acid, a sulfonic acid, and a phosphonic acid.

* * * * *